(12) United States Patent
Fenrich

(10) Patent No.: US 11,600,106 B2
(45) Date of Patent: Mar. 7, 2023

(54) SYSTEMS AND METHODS FOR GENERATING THREE-DIMENSIONAL IMAGES OF AN OBJECT BASED ON FRUSTRATED TOTAL INTERNAL REFLECTION

(71) Applicant: Identification International, Inc., Blacksburg, VA (US)

(72) Inventor: Richard Karl Fenrich, Blacksburg, VA (US)

(73) Assignee: Identification International, Inc., Blacksburg, VA (US)

( * ) Notice: Subject to any disclaimer, the term of this patent is extended or adjusted under 35 U.S.C. 154(b) by 22 days.

(21) Appl. No.: 17/599,635

(22) PCT Filed: Mar. 30, 2020

(86) PCT No.: PCT/US2020/025770
§ 371 (c)(1),
(2) Date: Sep. 29, 2021

(87) PCT Pub. No.: WO2020/205766
PCT Pub. Date: Oct. 8, 2020

(65) Prior Publication Data
US 2022/0165086 A1    May 26, 2022

Related U.S. Application Data

(60) Provisional application No. 62/826,586, filed on Mar. 29, 2019.

(51) Int. Cl.
*G06K 9/00*      (2022.01)
*G06V 40/12*     (2022.01)
(Continued)

(52) U.S. Cl.
CPC .......... *G06V 40/1359* (2022.01); *G06V 10/28* (2022.01); *G06V 10/60* (2022.01); *G06V 10/771* (2022.01)

(58) Field of Classification Search
None
See application file for complete search history.

(56) References Cited

U.S. PATENT DOCUMENTS

| 5,715,059 A | 2/1998 | Guerra |
| 5,812,252 A | 9/1998 | Bowker |
| (Continued) | | |

FOREIGN PATENT DOCUMENTS

WO        2008017077        2/2008

OTHER PUBLICATIONS

International Patent Application No. PCT/US2020/025//0, International Search Report and Written Opinion dated Jun. 18, 2020, 11 pages.

(Continued)

*Primary Examiner* — Avinash Yentrapati
(74) *Attorney, Agent, or Firm* — Sheppard Mullin Richter & Hampton LLP

(57) ABSTRACT

Systems and methods for generating a three-dimensional representation of a surface using frustrated total internal reflection. The system may obtain a two-dimensional image of an object in close proximity to an imaging surface. The intensity of the electromagnetic radiation received for individual points on the object may be determined. The system may determine a distance between the imaging surface and the object at each of the individual points based on a correlation between the electromagnetic radiation transmitted towards the imaging surface and the electromagnetic radiation reflected from the imaging surface. The determined intensity of the electromagnetic radiation may indi- (Continued)

cate the electromagnetic radiation reflected from the imaging surface. A three-dimensional representation of the object may be generated based on the two-dimensional image and/or the determined distances between the imaging surface and the object at each of the individual points.

16 Claims, 5 Drawing Sheets

(51) Int. Cl.
*G06V 10/771* (2022.01)
*G06V 10/60* (2022.01)
*G06V 10/28* (2022.01)

(56) References Cited

U.S. PATENT DOCUMENTS

| | | | |
|---|---|---|---|
| 6,122,394 A | 9/2000 | Neukermans | |
| 7,880,891 B1 | 2/2011 | Kim | |
| 8,797,028 B2 | 8/2014 | Verschuren | |
| 2007/0165914 A1 | 7/2007 | Werthiem | |
| 2008/0025580 A1 | 1/2008 | Sidlauskas | |
| 2011/0096025 A1 | 4/2011 | Slobodin | |
| 2013/0202182 A1 | 8/2013 | Rowe | |
| 2016/0078270 A1* | 3/2016 | Lee | G06V 40/1359 382/125 |
| 2016/0092718 A1 | 3/2016 | Jensen | |
| 2016/0292491 A1 | 10/2016 | Dickerson | |
| 2017/0169282 A1 | 6/2017 | Hogan | |
| 2018/0107852 A1* | 4/2018 | Fenrich | G06V 40/1306 |
| 2018/0225498 A1 | 8/2018 | Setlak | |
| 2018/0330136 A1 | 11/2018 | Fenrich | |
| 2019/0164292 A1 | 5/2019 | Fenrich | |
| 2019/0362120 A1* | 11/2019 | Yeke Yazdandoost | H01L 27/14629 |
| 2020/0372656 A1* | 11/2020 | Fenrich | G06V 40/1347 |

OTHER PUBLICATIONS

Zhu, S., et al., "Frustrated Total Internal Reflection: A Demonstration and Review", American Journal of Physics, vol. 54, No. 7, Jul. 1986, copyright 1986 American Association of Physics Teachers, pp. 601-607.

\* cited by examiner

SYSTEMS AND METHODS FOR GENERATING THREE-DIMENSIONAL IMAGES OF AN OBJECT BASED ON FRUSTRATED TOTAL INTERNAL REFLECTION

CROSS-REFERENCE TO RELATED APPLICATION

This application is a National Phase application under 35 U.S.C. § 371 of PCT Application No. PCT/US2020/025770, filed Mar. 30, 2020, which application claims the benefit of U.S. Provisional Patent Application Ser. No. 62/826,586, filed Mar. 29, 2019, entitled "SYSTEMS AND METHODS FOR GENERATING THREE-DIMENSIONAL IMAGES OF AN OBJECT BASED ON THE FRUSTRATED TOTAL INTERNAL REFLECTION", which are hereby incorporated herein by reference in their entirety.

FIELD OF THE INVENTION

The systems and methods described herein relate to generating three-dimensional images of an object by measuring the amount of light that is reflected from an imaging surface as potentially reduced, in part, by frustrated total internal reflection.

BACKGROUND

In forensic science, fingerprints have been used as a form of identification for centuries. Fingerprints (i.e., friction ridge signatures) illustrate a pattern of friction ridges and valleys having features that may be identified. Conventional fingerprint imaging technology generates two-dimensional images in which the top of the friction ridges are typically represented by varying gray scale values in the image. The gray scale variation of these friction ridges that make up the friction ridge pattern is due, in part, to the fingerprint ridge being physically like a mountain range, undulating up and down with areas of lower relative elevation and areas where peaks exist. Often, these variations are not obvious or visible in typical two-dimensional fingerprint representations and this may lead to conventional fingerprint imaging technology acceptance of spoofed, or faked fingerprints, through the use of silicon fingers cast from real people, high-resolution prints on transparent slides, and/or other forms of artificial fingerprints.

Using imaging surfaces to identify patterns or variations is a helpful or necessary endeavor in other fields as well. However, like conventional fingerprint imaging technology, the two-dimensional images typically generated can often be imprecise, unable to detect small surface variations, and/or easily circumvented. As such, there is a need for a means to generate high-resolution three-dimensional images of surfaces that include variations not visible in two-dimensional images.

SUMMARY

The systems and methods described herein relate to a novel device configured to generate a three-dimensional image of an object located on or in close proximity to an imaging surface. At its basic level, a three-dimensional image is a set of points located in three-dimensional space and this image may have different representations. Specifically, the systems and methods described herein relate to creating a three-dimensional image of an object by capturing a two-dimensional image of an object, determining, for various points on the object, the distance from the imaging surface to a portion of the object on a third spatial axis, and generating a three-dimensional image of the object using the two-dimensional image of the object and the determined distances in the third dimension. As described herein, the x-y plane is the planar surface formed by two orthogonal axes (the x- and y-axes) that the imaging surface may have. The z-axis is orthogonal to the x- and y-axes. There is no need for the imaging surface to be flat as long as Snell's Law and the Fresnel relations apply for that surface. For example, the object may comprise a fingerprint having ridges and valleys, and the systems and methods described herein may be configured to determine the distance between the imaging surface and these undulating areas in order to generate a three-dimensional image of the fingerprint. In various implementations, the systems described herein may include a TIR-based imaging system. The TIR-based imaging system may include at least a radiation source (such as light source), glass or a prism having an imaging surface, and a sensor device (such as a camera) positioned to receive the electromagnetic radiation transmitted by the radiation source toward the imaging surface which reflects the electromagnetic radiation toward the sensor. The electromagnetic radiation may comprise infrared light, visible light, ultraviolet light, electricity, and/or any other wavelength of electromagnetic radiation that obeys the Snell's Law and the Fresnel relations.

In order to generate three-dimensional images (or representations) of the object, the distances between the object and the imaging surface are determined by measuring the amount of light reflected from the imaging surface. Under total internal reflection, substantially all of the incident light could be reflected, but when an object is in contact or in close proximity to the imaging surface, some of the incident radiation is transmitted across the imaging surface and thus, the amount of reflected radiation decreases. In various implementations, light (or another form of electromagnetic radiation) may be transmitted through a first material (i.e., the glass or prism) to the imaging surface. As the light passes from the first material to a second material (e.g., air) at the imaging surface, a change in the speed of the light results in refraction. At a critical angle of incidence, the refracted light becomes totally internally reflected. When total internal reflection occurs, a standing and exponentially decaying surface wave called an evanescent wave propagates on the imaging surface. Since this evanescent wave contains no net energy, all incident light energy is reflected back into the first material—this process is called total internal reflection (TIR). When an object is brought near the imaging surface but not touching, total internal reflection is disturbed (or frustrated) and some of the light is transmitted to the object via the evanescent wave, thereby reducing the reflected power at the surface. This reduction in reflected power may be captured by a camera. Based on the reduced light that is reflected, the object to imaging surface distance may be determined. In various implementations, the combination of a two-dimensional image of the object and the determined object to imaging surface distance at various points along the imaging surface may be used to generate a three-dimensional image of the object surface.

In various implementations, the system described herein may include at least an imaging system (e.g., a TIR-based imaging system) and one or more physical processors. The one or more physical processors may be configured by computer-readable instructions. Executing the computer-readable instructions may cause the one or more physical processors to determine the distance between various points on an object and an imaging surface and generate a three-dimensional image of the object based on a two-dimensional image of the object and the determined distances between an imaging surface and the object. The computer-readable instructions may include one or more computer program components. The computer program components may include one or more of an information component, a distance determination component, an image generation component, a spoof detection component, and/or other computer program components. In some implementations, an imaging system and the one or more physical processors may be included with a single device configured to generate high-resolution three-dimensional images. The one or more physical processors may represent processing functionality of multiple components of the system operating in coordination. Therefore, the various processing functionality described in relation to the one or more processors may be performed by a single component or by multiple components of the system.

The information component may be configured to obtain information necessary to generate a three-dimensional image (or representation) of an object. In various implementations, the object may comprise a fingerprint or other human or animal skin. However, the object is not limited to a fingerprint or other skin as the systems and methods described herein may be used to generate a three-dimensional image of any object that can be brought within close proximity to the imaging surface. For example, the systems and methods described herein may be used to generate a three-dimensional image of any object comprising at least one uneven surface. In various implementations, the information obtained may comprise at least a two-dimensional image of the object generated based on electromagnetic radiation reflected from an imaging surface and received by a sensor device of an imaging system. For example, the electromagnetic radiation may comprise light transmitted in a TIR-based imaging system towards an imaging surface which reflects the light toward a sensor device. The sensor device may comprise a camera positioned to receive the light reflected from the imaging surface. In various implementations, the information component may be configured to cause the information obtained to be provided to the distance determination component, the image generation component, and/or other components of the system.

The distance determination component may be configured to determine the distance between the imaging surface and the object at each of a series of individual points on the object. In various implementations, the distance determination component may be configured to determine the distance between the imaging surface and the object by measuring the amount of light that is reflected from the imaging surface proximate to the object. In other words, the distance determination component may be configured to determine the distance between the imaging surface and the object based on a correlation between the electromagnetic radiation transmitted towards the imaging surface and the electromagnetic radiation reflected from the imaging surface. In various implementations, the distance determination component may be configured to determine an intensity of the electromagnetic radiation that is received by the sensor corresponding to individual points on the object. The intensity of the electromagnetic radiation that is received may be determined based on the two-dimensional image of the object. For example, in a TIR-based imaging system, the intensity of the light that is reflected from the imaging surface that correspond to individual points on the object may be determined based on the camera response in the TIR-based imaging system. Based on the determined intensity of the electromagnetic radiation received and known values for the index of refraction of the prism (or other media through which the electromagnetic radiation is propagated), the index of refraction of the media between the prism and object, the index of refraction of the object, the angle of incidence at the first interface, and the wavelength of the radiation transmitted towards the imaging surface, the distance determination component may be configured to determine the distance between the imaging surface and the object.

The image generation component may be configured to generate a three-dimensional image (or representation) of the object. For example, the image generation component may be configured to generate a three-dimensional representation of the object based on the two-dimensional image of the object and the determined distances between the imaging surface and the object at each of a series of individual points. In some implementations, the image generation component may be configured to map the determined distances between the imaging surface and the object to the two-dimensional image of the object. For example, the image generation component may be configured to generate a uniform point cloud indicating distances from the imaging surface to the object for each of a series of points on the object by adding a third spatial dimension to the two-dimensional image of the object. In various implementations, the three-dimensional image (or representation of the object) may comprise a three-dimensional image (or representation) of a surface of the object.

The spoof detection component may be configured to determine whether or not an image of an object (such as a fingerprint image) is real or fake. For example, the spoof detection component may be configured to segment a three-dimensional image based on the uniform point cloud and identify features of the object within the image.

In various implementations, the spoof detection component may be configured to extract measurements of the features in both in the x-y plane, as well as along the z-axis. For example, as measurements are extended from planes parallel to the x-y axis into the z-axis, the height, average height, distance from the platen, volume, surface area, and other geometric measurements of the features that relate to the z-axis representation may be measured. In various implementations, the spoof detection component may be configured to collect the feature measurements for each of the various features in an image and bin them to create a distribution of the various features across the image. In some implementations, the spoof detection component may be configured to generate a histogram of the distance of the z-level of the contours around a feature to the scanning surface. In an example implementation involving images of fingerprints, the distribution of this histogram may be bell shaped in the case of a real fingerprints and non-bell shaped in the case of fake fingerprints. In some implementations, the spoof detection component may be configured to input the binned measurements into a neural network, or a linear discriminator, with advance knowledge of the spoof or not-spoof nature of the input. The neural network or linear discriminator may be trained with a set of exemplars and then used to automatically classify these histograms to provide information about whether or not the image is real or fake.

As used herein, a point may be a section and/or area of an object which, in the context of the resolution of the imaging system, can be considered a single position in three-dimensional space. When referring to a point on an object, the location of that point may depend on the context of the discussion. A point on an object may refer to the actual location of the point on the object, and/or it may refer to the location on the imaging surface manifested by the point on the object through the imaging system.

These and other objects, features, and characteristics of the system and/or method disclosed herein, as well as the methods of operation and functions of the related elements of structure and the combination thereof, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The drawings are provided for purposes of illustration only and merely depict typical or example implementations. These drawings are provided to facilitate the reader's understanding and shall not be considered limiting of the breadth, scope, or applicability of the disclosure. For clarity and ease of illustration, these drawings are not necessarily drawn to scale.

DETAILED DESCRIPTION

Figure 1:
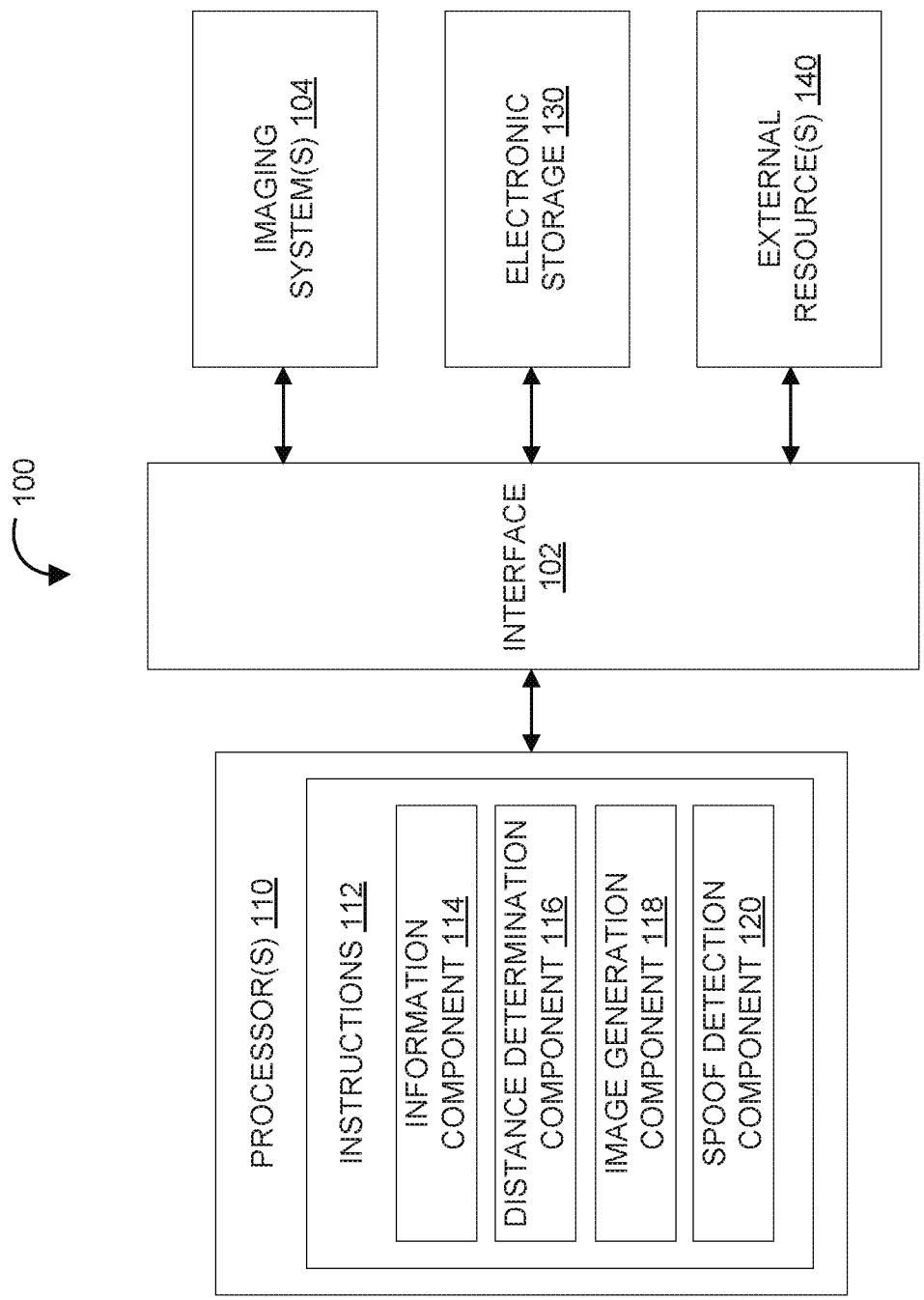
FIG. 1 illustrates a system configured to generate a three-dimensional image of an object based on two-dimensional imaging of the object and a determined object to imaging surface distance at various points along the object, in accordance with one or more implementations.

FIG. 1 illustrates a system 100 configured to generate a three-dimensional image of an object based on two-dimensional imaging of the object and a determined object to imaging surface distance at various points along the object, in accordance with one or more implementations. At its basic level, a three-dimensional image is a set of points located in three-dimensional space and this image may have different representations. In various implementations, the system may be configured to determine the distance between the object and the imaging surface by measuring the amount of light that is reflected from the imaging surface after light transmitted due to broken total internal reflection (or TIR) and frustrated total internal reflection has been removed. Under TIR, substantially all of the incident light could be reflected, but when an object is in contact or in close proximity to the imaging surface, some of the incident radiation is transmitted across the imaging surface and thus, the amount of reflected radiation decreases.

The system may include one or more of interface 102, imaging system(s) 104, physical processor(s) 110, electronic storage 130, external resource(s) 140, and/or other components. In some implementations, one or more imaging systems 104 and one or more physical processors 110 may be included within a single device configured to generate high-resolution three-dimensional images.

In various implementations, one or more imaging systems 104 (also interchangeably referred to herein as imaging system(s) 104, imaging system 104, or imaging systems 104 for convenience) may include a live scan imaging system. For example, imaging system(s) 104 may include one or more of a total internal reflection based imaging system (i.e., TIR-based imaging system), a electroluminescent imaging system, an ultrasound scanner, a three-dimensional scanner, a capacitive array imaging system, thermal sensor imaging systems, radio frequency (RF) imaging systems, pressure sensor imaging systems, other optical sensor imaging systems, and/or other systems. In various implementations, imaging system(s) 104 may comprise a TIR-based imaging system (e.g., TIR-based imaging system 200).

By way of non-limiting example, total internal reflection is a known concept derived from light traveling at different speeds in different materials. A refractive index ($n_i$) of a material (i,) is the speed of light in a vacuum ($c_i$) divided by the velocity of light in the material ($v_i$):

$$n_i = c/v_i.$$

As light passes from one material to another, the change of speed results in refraction. Measured from a perpendicular to the surface boundary between two materials, the angle of incidence ($\theta_1$) and the angle of refraction ($\theta_2$) are given by Snell's law:

$$n_1 \sin(\theta_1) = n_2 \sin(\theta_2).$$

Accordingly, when light emerges from a glass block ($n_1$~1.5) into air ($n_2$=1), the light will be refracted away from the perpendicular to the surface. That is, $\theta_2 > \theta_1$ because $n_1 > n_2$. At a critical angle of incidence ($\theta_c$), $\theta_2$ becomes 90°. At this angle or any greater angle contained within the transmitting media, all light is internally reflected back into the first media and an exponentially decaying standing wave propagates along the imaging surface as an evanescent wave. When $\theta_1 > \theta_c$, the incident light is reflected back into the glass by total internal reflection (TIR). Changes in TIR may serve to generate an image of a finger applied to the imaging surface. The intensity of light reflected from the imaging surface at a particular location may be altered according to several optical mechanisms. For example, touching or placing a finger or other material in close proximity to the imaging surface may absorb or scatter the refracted ray or couple with the evanescent wave, thus causing light to be transmitted across the imaging surface boundary.

TIR-based imaging systems are generally known in the art. Such systems have been developed to capture images of fingerprints using a prism (e.g., glass or plastic). TIR-based imaging systems typically comprise a radiation source (e.g., a light source or other radiation source), a platen, waveguide, optical fiber, prism, or other media within which TIR may occur having an imaging surface, and a sensor device positioned to receive the electromagnetic radiation that is reflected from the imaging surface. In some implementations, the electromagnetic radiation may comprise infrared light, visible light, ultraviolet light, electricity, and/or any other wavelength of electromagnetic radiation that obeys the Snell's Law and the Fresnel relations as described herein.

Figure 2:
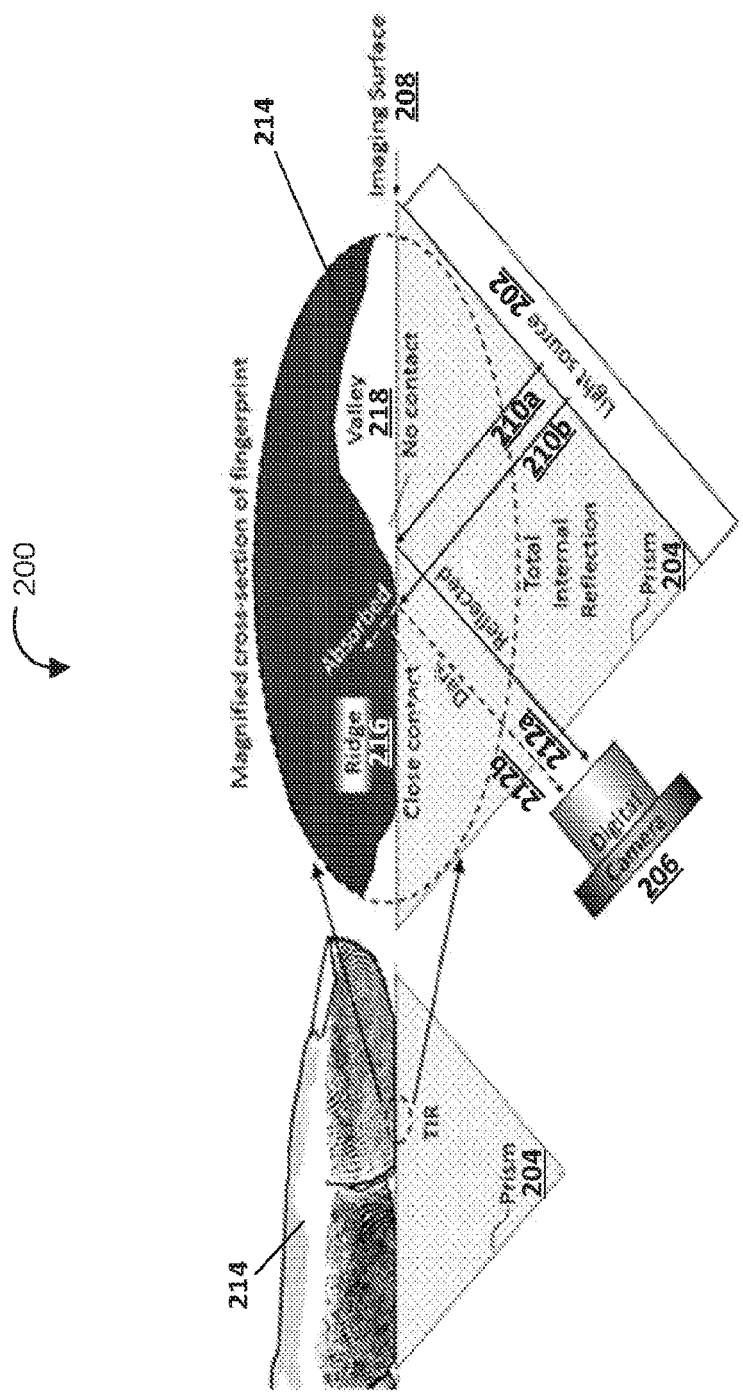
FIG. 2 illustrates a TIR-based imaging system, in accordance with one or more implementations.

FIG. 2 illustrates a TIR-based imaging system 200, in accordance with one or more implementations. In various implementations, TIR-based imaging system 200 may comprise at least a light source 202, a prism 204, and a camera 206. In some implementations, light source 202 may be replaced by another type of radiation source. Prism 204 may comprise a platen, a waveguide, a prism, and/or any other media through which electromagnetic radiation may be propagated through via transmission. For example, prism 204 may comprise a prism through which light beams in a TIR-based imaging system are directed and/or reflected. Prism 204 may include imaging surface 208 at which light source 202 is directed. Camera 206 may comprise a digital camera and/or other sensor device configured to receive or capture the electromagnetic radiation that is reflected from imaging surface 208. In various implementations, camera 206 may be configured to capture a two-dimensional image of the object based on the received electromagnetic radiation that is reflected from imaging surface 208. For example, generating two-dimensional images of an object with a TIR-based imaging system in general is known. Camera 206 of TIR-based imaging system 200 may be configured to capture a two-dimensional image of the object as is known in the art.

In various implementations, light from light source 202 (i.e., transmitted light 210a and 210b) is transmitted toward a face of prism 204 at an angle greater than the critical angle. Incident angles beyond the critical angle will cause an evanescent wave to form on the imaging surface 208 and the propagating light to totally internally reflect in the prism and pass out through the opposing side. Camera 206 may be positioned on a side of prism 204 (i.e., the opposing side) to capture the light that is reflected (i.e., reflected light 212a and 212b) from imaging surface 208. When an object (e.g., finger 214) is placed in close proximity to imaging surface 208 (e.g., the prism face where TIR occurs), it changes the boundary conditions such that where friction ridges make contact with imaging surface 208 (e.g., at ridge 216), the light from light source 202 (i.e., transmitted light 210b) is transmitted and largely attenuated by the skin. The amount of light transmitted and reflected obeys the Fresnel relations. Where the friction ridges do not make contact (e.g., at valley 218), the light from light source 202 (i.e., transmitted light 210a) is totally internally reflected by the interface and captured by a camera or sensor 206, which may be oriented to view the surface from the reflection angle matching the source angle of incidence. Light scattered or absorbed by the finger reduces the local light intensity in an image captured by the camera or the sensor 206. The result is high contrast two-dimensional fingerprint images from the prism surface scene such that the background appears light and a fingerprint (i.e., friction ridge signature) appears dark since the TIR is broken by the friction ridges. Thus far, contact with the imaging surface and non-contact with the surface beyond a small distance have been considered within FIG. 2. The case of non-contact but within close proximity is considered in the description of FIG. 3. As described further herein, the distance between imaging surface 208 and a point on object 214 may also be determined based on the intensity of the radiation (or light) that is captured by camera or sensor 206 (i.e., the radiation that is reflected).

In some implementations, imaging system(s) 104 may comprise a TIR-based imaging system that includes a pressure sensitive membrane. For example, imaging system(s) 104 (e.g., TIR-based imaging system 200) may include a pressure sensitive membrane comprising a top surface, a bottom surface opposite the top surface, and an elastic deformable film forming at least a portion of the top surface. The pressure sensitive membrane may include light absorbing material to block ambient light. Accordingly, the systems and methods described herein for generating a three-dimensional image of an object may utilize a TIR-based imaging system that includes a pressure sensitive membrane. In some implementations, imaging system(s) 104 may be configured to capture two-dimensional images of objects using a pressure sensitive membrane. For example, imaging system(s) 104 may be configured to capture two-dimensional images of objects using a pressure sensitive membrane as described in U.S. patent application Ser. No. 15/091,532, entitled "SYSTEMS AND METHODS FOR CAPTURING IMAGES USING A PRESSURE SENSITIVE MEMBRANE," the disclosure of which is hereby incorporated by reference in its entirety herein. In some implementations, the systems and methods described herein may be configured to identify features of a friction ridge signature of a subject based on information representing topography of friction ridges. For example, the systems and methods described herein may be configured to identify features of a friction ridge signature of a subject as described in U.S. patent application Ser. No. 15/724,054, entitled "SYSTEM AND METHOD FOR IDENTIFYING FEATURES OF A FRICTION RIDGE SIGNATURE BASED ON INFORMATION REPRESENTING A TOPOGRAPHY OF FRICTION RIDGES," the disclosure of which is hereby incorporated by reference in its entirety herein.

Returning back to FIG. 1, the one or more physical processors 110 (also interchangeably referred to herein as processor(s) 110, processor 110, or processors 110 for convenience) may be configured to provide information processing capabilities in system 100. As such, the processor(s) 110 may comprise one or more of a digital processor, an analog processor, a digital circuit designed to process information, a central processing unit, a graphics processing unit, a microcontroller, an analog circuit designed to process information, a state machine, and/or other mechanisms for electronically processing information.

Processor(s) 110 may be configured to execute one or more computer readable instructions 112. Computer readable instructions 112 may include one or more computer program components. In some implementations, computer readable instructions 112 may be stored in electronic storage 130. Computer readable instructions 112 may include one or more of information component 114, distance component 116, image generation component 118, spoof detection component 120, and/or other computer program components. As used herein, for convenience, the various computer readable instructions 112 will be described as performing an operation, when, in fact, the various instructions program the processor(s) 110 (and therefore system 100) to perform the operation.

Information component 114 may be configured to obtain information necessary to generate a three-dimensional image (or representation) of an object. In various implementations, Information component 114 may be configured to obtain at least a two-dimensional image of an object generated based on electromagnetic radiation reflected from an imaging surface. The two-dimensional image may comprise a two-dimensional image of an object in contact with, or in close proximity to, an imaging surface. In various implementations, the two-dimensional image may be generated based on electromagnetic radiation reflected from the imaging surface and received by a sensor device of an imaging system. For example, information component 114 may be configured to obtain the two-dimensional image of an object from a camera of imaging system 104 (e.g., camera 206 of TIR-based imaging system 200). As described further herein, the sensor output of the sensor device (e.g., the camera response of camera 206) may be used by distance determination component 116 to determine the intensity of the radiation (or light) that is reflected from the imaging surface and determine the distance of various points on an object from the imaging surface based on the intensity of the light at corresponding points in the two-dimensional image. The two-dimensional image of the object and the determined distances in the third dimension may be used to generate a three-dimensional image (or representation) of the object. In various implementations, information component 114 may be configured to cause the information necessary to generate a three-dimensional image (or representation) of an object to be communicated to one or more other components of system 100. For example, information component 114 may be configured to cause the two-dimensional image of the object obtained from a sensor device of imaging system 104 to be provided to distance determination component 114.

Distance determination component 116 may be configured to determine a distance between an imaging device and an object at a series of points on the object. For example, distance determination component 116 may be configured to determine the distance between the imaging device and an object at a series of points on the object that are spaced a predetermined distance from one another. In various implementations, distance determination component 116 may be configured to determine the distance between an imaging surface and an object by measuring the amount of light that is reflected from the imaging surface proximate to the object. For example, distance determination component 116 may be configured to determine the distance between the imaging surface and the object based on a correlation between the electromagnetic radiation transmitted towards the imaging surface and the electromagnetic radiation reflected from the imaging surface. In various implementations, distance determination component 116 may be configured to determine an intensity of the electromagnetic radiation that is received by the sensor corresponding to individual points on the object. The intensity of the electromagnetic energy that is received may be determined based on the two-dimensional image of the object. Based on the determined intensity of the electromagnetic energy received and known values for the index of refraction of the prism (or other media through which the electromagnetic energy is propagated), the index of refraction of the media between the prism and object, the index of refraction of the object, the angle of incidence at the first interface, and the wavelength of the energy transmitted towards the imaging surface, distance determination component 116 may be configured to determine the distance between the imaging surface and the object.

In various implementations, distance determination component 116 may be configured to determine a distance between an imaging surface and a point on an object by measuring the amount of light that is reflected from the imaging surface as reduced by transmission of light across the imaging surface boundary due to breaking of the total internal reflectance and frustrated total internal reflection. Frustrated total internal reflection (FTIR) directly relates to total internal reflection (TIR). When TIR occurs, the preponderance of the electromagnetic radiation (e.g., light waves) reflected from an interface (e.g., imaging surface 208) are captured by a sensor (e.g., a camera). When TIR is "broken" or FTIR occurs, a portion of the electromagnetic radiation is transmitted across the imaging surface (i.e., the interface between the prism and media on the other side of the surface). Accordingly, the electromagnetic radiation captured by the sensor is reduced because the energy reflected from the imaging surface is reduced as a result of the radiation being transmitted to the object in contact or close proximity with the imaging surface.

When the interface formed by a first media and a second media is flat and isotropic, the amount of light transmitted and reflected are given by the Fresnel relations as a ratio of the transmitted (and reflected) amplitudes to the incident amplitude. These relations, derivable from Maxwell's equations, provide the reflection and transmission coefficients in the s and p polarizations at the interface (e.g., at imaging surface 208). In the equations below for the incident wave, r is the reflected component and t is the transmitted component while the subscripts represent s or p polarization. In addition, $n_1$ is the index of refraction of media 1, $\theta_i$ is the incident angle, $n_2$ is the index of refraction of media 2, and $\theta_t$ is the refracted angle. These equations apply to the interface between two media:

$$r_s = \frac{n_1 \cos\theta_i - n_2 \cos\theta_t}{n_1 \cos\theta_i + n_2 \cos\theta_t},$$

$$t_s = \frac{2n_1 \cos\theta_i}{n_1 \cos\theta_i + n_2 \cos\theta_t},$$

$$r_p = \frac{n_2 \cos\theta_i - n_1 \cos\theta_t}{n_2 \cos\theta_i + n_1 \cos\theta_t},$$

$$t_p = \frac{2n_1 \cos\theta_i}{n_2 \cos\theta_i + n_1 \cos\theta_t}.$$

The Fresnel relations rely on the incident angle, the refracted angle, and the indices of refraction on both sides of the interface. Accordingly, the Fresnel relations rely on the same variables that appear in Snell's Law.

In an example implementation in which imaging system 104 comprises TIR-based imaging system 200, three media may be involved in the transmission, absorption, and/or reflection of radiation transmitted by the radiation source—prism 204 (media 1), the media between prism 204 and object 214 (media 2), and object 214 (media 3). Each of these media has an index of refraction. For example, $n_1$ is the index of refraction of media 1, $n_2$ is the index of refraction of media 2, and $n_3$ is the index of refraction of media 3. In some implementations, media 2 (i.e., the media between prism 204 and object 214) is not air with an index of refraction equal to 1.0. In some implementations, media 2 may comprise any media at which TIR may occur between media 1 and media 2.

Without the third media, at an angle of incidence greater that the critical angle for the media 1 and media 2 interface, light propagating toward the imaging surface 208 is totally internally reflected and a non-energy transferring evanescent wave propagates on the imaging surface. The full incident beam would be reflected as a result of TIR. However, the full incident beam would not be reflected when an object is close enough to the interface such that it couples with the evanescent wave. For example, when the third media (object 214) is in close enough proximity to the interface, the evanescent wave couples with the third media, causing a portion of the incident light to be transmitted to the object. Such a location is indicated at point A in FIG. 3, whereas point B is sufficiently distant to imaging surface 208 so that TIR is maintained at that point. As a result, there is a reduction in reflected light intensity due to this transmission of light across the boundary. This phenomenon is known as frustrated total internal reflection (or FTIR).

Figure 3:
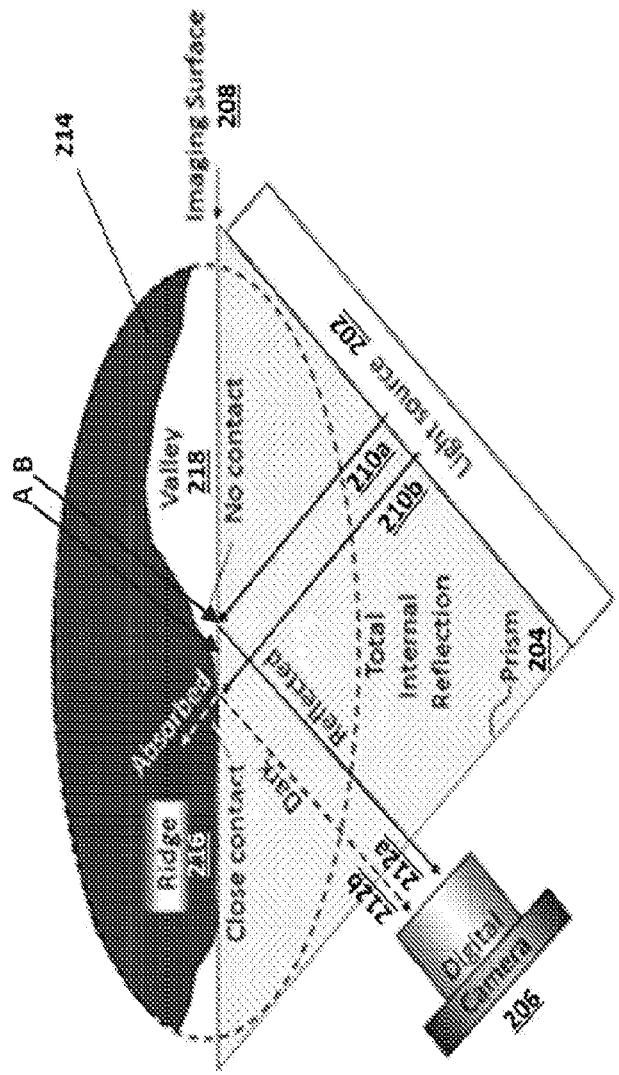
FIG. 3 illustrates the occurrence of frustrated total internal reflection in a TIR-based imaging system, in accordance with one or more implementations.

FIG. 3 illustrates the occurrence of frustrated total internal reflection in a TIR-based imaging system, in accordance with one or more implementations. At Point B, TIR would cause the full incident beam to be reflected because valley 218 is not within close enough proximity to the interface. However, at Point A, FTIR would result in less than the full incident beam to be reflected because ridge 216 is within a close enough proximity to the interface to cause a portion of the incident light to be transmitted to object 214 via evanescent wave coupling.

Referring back to FIG. 1, distance determination component 116 may be configured to determine the distance between an imaging surface and a point on an object in close proximity to the imaging surface based on the intensity of the radiation (or light) that is reflected from the imaging surface. In various implementations, distance determination component 116 may be configured to determine the distance between the imaging surface and a point on the object based on the intensity of the radiation (or light) that is captured by a sensor device (i.e., the radiation that is reflected). For example, the sensor device may comprise a camera (e.g., camera 206) and/or other device configured to capture and/or receive electromagnetic radiation reflected from an imaging surface. In various implementations, distance determination component 116 may be configured to determine a distance between the imaging surface and a point on the object based on a correlation between the electromagnetic radiation transmitted towards the imaging surface and the reflected electromagnetic radiation that is captured by the sensor device.

In various implementations, distance determination component 116 may be configured to determine the intensity of electromagnetic radiation that is received for each of a series of individual points on an object. In various implementations, distance determination component 116 may be configured to determine the intensity of the radiation that is reflected from the imaging surface based on a sensor output of a sensor device. For example, distance determination component 116 may be configured to determine the intensity of the light that is reflected from the imaging surface at individual points on the object based on the camera response of camera (e.g., camera 206) of a TIR-based imaging system (e.g., TIR-based imaging system 200).

In various implementations, distance determination component 116 may be configured to determine the distance between the imaging surface and a point on the object based on the intensity of the radiation (or light). For example, distance determination component 116 may obtain and/or store an indication of the index of refraction ($n_1$) of media 1 (i.e., the prism), the index of refraction ($n_2$) of media 2, the index of refraction ($n_3$) of media 3 (i.e. the finger), the angle of incidence ($\theta_1$), and the wavelength ($\lambda$) of the radiation transmitted by the radiation source towards the imaging surface. Based on these stored values and the determined intensity of the radiation (or light), distance determination component 116 may be configured to determine the distance between the imaging surface and a point on the object by determining the distance (d) between the interface formed by the prism and the media on the other side of the imaging surface based on the following equations:

$$T=1-|r|^2 \text{ for both the } s \text{ and } p \text{ polarizations.}$$

$$1/T=\alpha \sinh^2 y + \beta$$

where $y=(2\pi d/\lambda)(n_{12}\sin^2\theta_1 - n_{22})^{1/2}$
and $\alpha$ and $\beta$ take the form of $\alpha_s$, $\alpha_p$, $\beta_s$ and $\beta_p$:

$$\alpha_s=[(N^2-1)(n^2N^2-1)]/[4N^2 \cos\theta_1(N^2\sin^2\theta_1-1)(n^2-\sin^2\theta_1)^{1/2}]$$

$$\beta_s=[(n^2-\sin^2\theta_1)^{1/2}+\cos\theta_1]^2/[4\cos\theta_1(n^2-\sin^2\theta_1)^{1/2}]$$

$$\alpha_p=(\alpha_s/n^2)[(N^2+1)\sin^2\theta_1-1][(n^2N^2+1)\sin^2\theta_1-n^2]$$

$$\beta_p=[(n^2-\sin^2\theta_1)^{1/2}+n^2\cos\theta_1]^2/[4n^2\cos\theta_1(n^2-\sin^2\theta_1)^{1/2}]$$

$$n=n_3/n_1$$

$$N=n_1/n_2$$

Notably, these calculations are based on the identity that T+R=1, where T is the transmitted power at an interface and R is the reflected power at the interface. This identity provides for the conservation of energy.

Using these equations, distance determination component 116 may be configured to determine a distance between the imaging surface and a point on the object within a fraction of a wavelength. In various implementations, distance determination component 116 may be configured to convert raw, unprocessed pixels of the object surface in the resultant image into an intensity by scaling the normalized pixel value by the dynamic range of this pixel. Mathematically, I=(p−b)/(w−b) where is intensity, p is the captured value of the pixel, b is the pixel value with no incident illumination, and w is the pixel value under unobstructed TIR. The b and the w values should be not, in general, be saturated. Based on T+R=1 and R=I, the equations above give $1/T=1/(1-I)=a \sinh^2 y + \beta$. With this value for I, distance determination component 116 may be configured to solve this equation for d—the distance between the imaging surface and the object. By iterating through a series of pixels in a captured image and solving for the distance value d at each pixel, distance determination component 116 may be configured to determine the distance between the imaging surface and the object at points across the object.

Image generation component 118 may be configured to generate a three-dimensional image of an object. In various implementations, image generation component 118 may be configured to generate a three-dimensional image of an object based on a two-dimensional image of the object and a determined distance of various points on the object from an imaging surface. Based on the distances determined, image generation component 118 may be configured to add a third dimension to the two-dimensional image of the object, thereby generating a three-dimensional rendering of the object. For example, image generation component 118 may be configured to map the determined distances between the imaging surface and the object to the two-dimensional image of the object. For example, image generation component 118 may be configured to generate a uniform point cloud indicating distances from the imaging surface to the object for each of a series of points on the object. Accordingly, by mapping the determined distances to the two-dimensional image of the object, image generation component 118 may be configured to generate a three-dimensional image of the object. In various implementations, the three-dimensional image (or representation of the object may comprise a three-dimensional image (or representation) of a surface of the object.

Figure 4B:
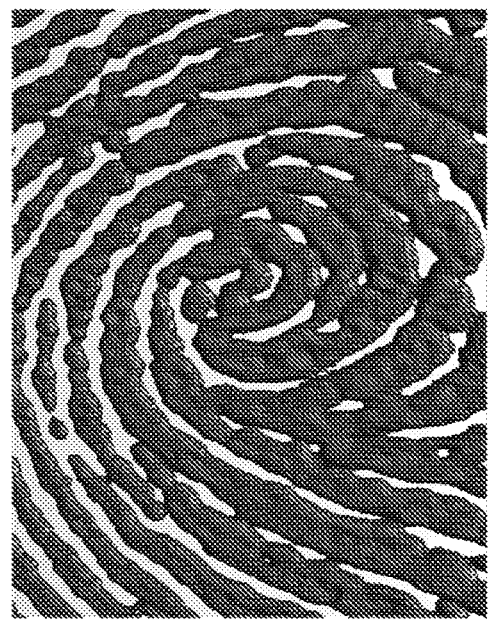
FIG. 4A and FIG. 4B depict example fingerprint images captured with different methods, in accordance with one or more implementations.
Figure 4A:

FIG. 4A and FIG. 4B depict example fingerprint images captured with different methods, in accordance with one or more implementations. FIG. 4A depicts an image 410 of a fingerprint captured in the standard two-dimensional manner by a live scan imaging system. FIG. 4B depicts an image 420 of a fingerprint in which only the 300 nanometers closest to the imaging surface are captured. In image 420, the primary wavelength of the light source was 545 nanometers and the angle of incidence of light at the interface was 45 degrees.

Spoof detection component 120 may be configured to detect fake objects (or fingerprints) based on the generation of a three-dimensional of the object. To generate a three-dimensional image of the object, a uniform point cloud indicating distances from the imaging surface to the object for each of a series of points on the object may be generated, as described herein. In various implementations, spoof detection component 120 may be configured to segment the image based on the uniform point cloud. For example, spoof detection component 120 may be configured to segment the image into a mesh based upon triangles and/or sophisticated features found in the three-dimensional image. One way to construct such a mesh is to take any four neighboring pixels in the two-dimensional image as depicted below and break this rectangle into two triangles as shown:

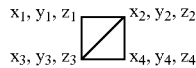

Each of the triangles is completely contained within a plane in three dimensions.

The ability to measure distances in the z axis at a much finer level than the x and y axes opens new possibilities for various applications. For example, a topic in fingerprint biometrics has been the detection of fake fingerprints, also called spoofs, to avoid granting access to a controlled resource. Nefarious actors may attempt to circumvent the proper use of a correct fingerprint. This attempt to fool a biometric system in this way is also known as a presentation attack. A closely related topic is liveness detection. If we know a finger is alive then certainly the finger would not be a fake finger made from silicone, for example. It would then be up to the fingerprint matching engine to determine if the finger was from a permissioned person.

As described herein, fingers have many features on them such as ridges, minutiae, incipient ridges, pores, lakes, and/or other features. Collectively, these features have been placed into three levels: level I, level II, and level III. Level I features may comprise loops, arches, tents, deltas, whorls, and/or other features. Level I features are mainly used to classify or subdivide fingerprints into broad categories and may not provide sufficient discriminating power to identify individuals, Level II features may comprise ridge endings, bifurcations, and dots. Level II features may provide the basis of present day fingerprint identification algorithms. Level III features include pores and have traditionally been harder to reliably detect and are smaller in size than the other classes, in general. If a feature, at any of these levels, can be identified and located within the fingerprint image, with the use of the three-dimensional images, more accurate measurements may be extracted in the x-y plane than traditional approaches, in addition to high-resolution measurements in the z-axis. For example, features such as perimeters, extents, and surface areas can be easily found by identifying contours of those features in a given z-plane and then measuring the features of the resulting contour. By using such measurements in multiple z-planes, changes of the metrics from one z-plane to the next may be measured using the techniques described herein. As measurements are extended from planes parallel to the x-y axis into the z-axis, the height, average height, distance from the platen, volume, surface area, and other geometric measurements of the features that relate to the z-axis representation may be measured. Some of these metrics will also incorporate elements of the x-y axes, such as volume.

For one or more pores, lakes, ridges, and/or other features of the object, spoof detection component 120 may be configured to measure the perimeter, surface area, extent, and/or other two-dimensional measures not only in planes parallel to the x-y plane, but also in any intersecting plane based on the three-dimensional mesh representation of the image. In some implementations, spoof detection component 120 may be configured to measure three-dimensional related metrics with respect to any plane, even those not parallel to the x-y plane. For example, these metrics may include heights, average heights over areas, volumes, average volumes, surface areas, and/or other geometric quantities associated with three-dimensional solids.

Pores often form cuplike structures. The volume of a pore may comprise the amount of water the pore may hold. To identify such pore candidates, the pore must necessarily have a bottom to it. From this bottom and the level at which the water will empty out of the pore, the contour at that water level may be calculated from the three-dimensional mesh. In various implementations, spoof detection component 120 may be configured to measure the distance of the contour to the imaging surface, the distance from the contour to the bottom of the pore, the volume of the water, and/or other geometrical features for each pore candidate. Note that other areas of the finger ridges have indentations as well that are not necessarily pores and these indentations can be found in the same way as the pore candidates are found above. Each of these features may be referred to as a pore candidate.

In various implementations, spoof detection component 120 may be configured to collect the feature measurements for each pore candidate in an image and bin them to create a distribution of the various features across the image. For example, spoof detection component 120 may be configured to take the percentage of the pore candidates in the image whose contour line is from 0 to 10 nanometers from the imaging surface and then from 11 to 20 nanometers and so on. In some implementations, spoof detection component 120 may be configured to generate a histogram of the distance of the z-level of the contours around a feature to the imaging surface. For pores, the distribution of this histogram may be bell-shaped in the case of real fingerprints and non-bell shaped in the case of fake fingerprints. In some implementations, spoof detection component 120 may be configured to use the distribution above within a pattern recognition paradigm, either supervised or unsupervised, by inputting the distribution into the pattern recognition paradigm. The goal of the pattern recognition engine can be to determine whether the input fingerprint is a spoof. For example, spoof detection component 120 may be configured to input binned measurements into a neural network, or a linear discriminator, with advance knowledge of the spoof or not spoof nature of the input. Using a known database of such examples, a training process may result in a configuration that will be reliably used to identify the underlying fingerprint as fake or real. For example, spoof detection component 120 may be configured to obtain and/or access known databases of such examples stored in electronic storage 130. In some implementations, the neural network or linear discriminator may be trained with a set of exemplars and then used to automatically classify these histogram to provide information about whether or not the image is real or fake. By undergoing supervised training of this system on a given training database, the training process will yield a trained system that can now take data from an unknown source to predict whether the fingerprint was a spoof or not. Many such approaches to discrimination analysis exist and the techniques described herein are not limited to any single approach, rather, the features that have been calculated from the high-resolution geometric data provide the basis for a novel classification approach.

The novelty of this approach is using the very high resolution of the three-dimensional images in the z-axis to perform much finer measurements than have ever been made before and to use these measurements to better analyze the image. The three-dimensional images generated by the systems and methods described herein will yield improved results over existing systems, including in the ability to better identify and use features related to the very high z-axis resolution.

Electronic storage 130 may include electronic storage media that electronically stores information. The electronic storage media of electronic storage 130 may be provided integrally (i.e., substantially non-removable) with one or more components of system 100 and/or removable storage that is connectable to one or more components of system 100 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may be a separate component within system 100, or electronic storage 130 may be provided integrally with one or more other components of system 100. Although electronic storage 130 is shown in FIG. 1 as a single entity, this is for illustrative purposes only. In some implementations, electronic storage 130 may comprise multiple storage units. These storage units may be physically located within the same device, or electronic storage 130 may represent storage functionality of multiple devices operating in coordination. In various implementations, electronic storage 130 may be configured to store software algorithms, information determined by processor 110, information received remotely, and/or other information that enables system 100 to function properly. For example, electronic storage 130 may store computer readable instructions 112.

In various implementations, imaging system 104 may include the one or more processor(s) 110. For example, imaging system 104 and processors 110 may be contained within a single self-contained device configured to generate a three-dimensional image of a surface by measuring the amount of light that is reflected from the imaging surface as potentially reduced, in part, by frustrated total internal reflection. External resources 140 may include sources of information, hosts and/or providers outside of system 100, external entities participating with system 100, and/or other resources.

Implementations of the disclosure may be made in hardware, firmware, software, or any suitable combination thereof. Aspects of the disclosure may be implemented as instructions stored on a machine-readable medium, which may be read and executed by one or more processors. A machine-readable medium may include any mechanism for storing or transmitting information in a form readable by a machine (e.g., a computing device). For example, a tangible computer readable storage medium may include read only memory, random access memory, magnetic disk storage media, optical storage media, flash memory devices, and others, and a machine-readable transmission media may include forms of propagated signals, such as carrier waves, infrared signals, digital signals, and others. Firmware, software, routines, or instructions may be described herein in terms of specific exemplary aspects and implementations of the disclosure, and performing certain actions.

Although imaging system 104, processor(s) 110, electronic storage 130, and external resources 140 are shown to be connected to interface 102 in FIG. 1, any communication medium may be used to facilitate interaction between any components of system 100. One or more components of system 100 may communicate with each other through hard-wired communication, wireless communication, or both. For example, one or more components of system 100 may be operatively linked via one or more electronic communication links. In some implementations, such electronic communication links may be established, at least in part, via a network 130 such as the Internet and/or other networks. It will be appreciated that this is not intended to be limiting, and that the scope of this disclosure includes implementations in which imaging system(s) 104, processor(s) 110, electronic storage 130, external resources 140, and/or other components may be operatively linked via some other communication media.

Although processor 110 is illustrated in FIG. 1 as a single component, this is for illustrative purposes only. In some implementations, processor 110 may comprise multiple processing units. These processing units may be physically located within the same device, or processor 110 may represent processing functionality of multiple devices operating in coordination. Processor 110 may be configured to execute one or more components by software; hardware; firmware; some combination of software, hardware, and/or firmware; and/or other mechanisms for configuring processing capabilities on processor 110.

Furthermore, it should be appreciated that although the various instructions are illustrated in FIG. 1 as being co-located within a single processing unit, in implementations in which processor(s) 110 include multiple processing units, one or more instructions may be executed remotely from the other instructions.

The description of the functionality provided by the different computer-readable instructions described herein is for illustrative purposes, and is not intended to be limiting, as any of instructions may provide more or less functionality than is described. For example, one or more of the instructions may be eliminated, and some or all of its functionality may be provided by other ones of the instructions. As another example, processor(s) 110 may be programmed by one or more additional instructions that may perform some or all of the functionality attributed herein to one of the computer-readable instructions.

Exemplary Flowcharts of Processes

Figure 5:
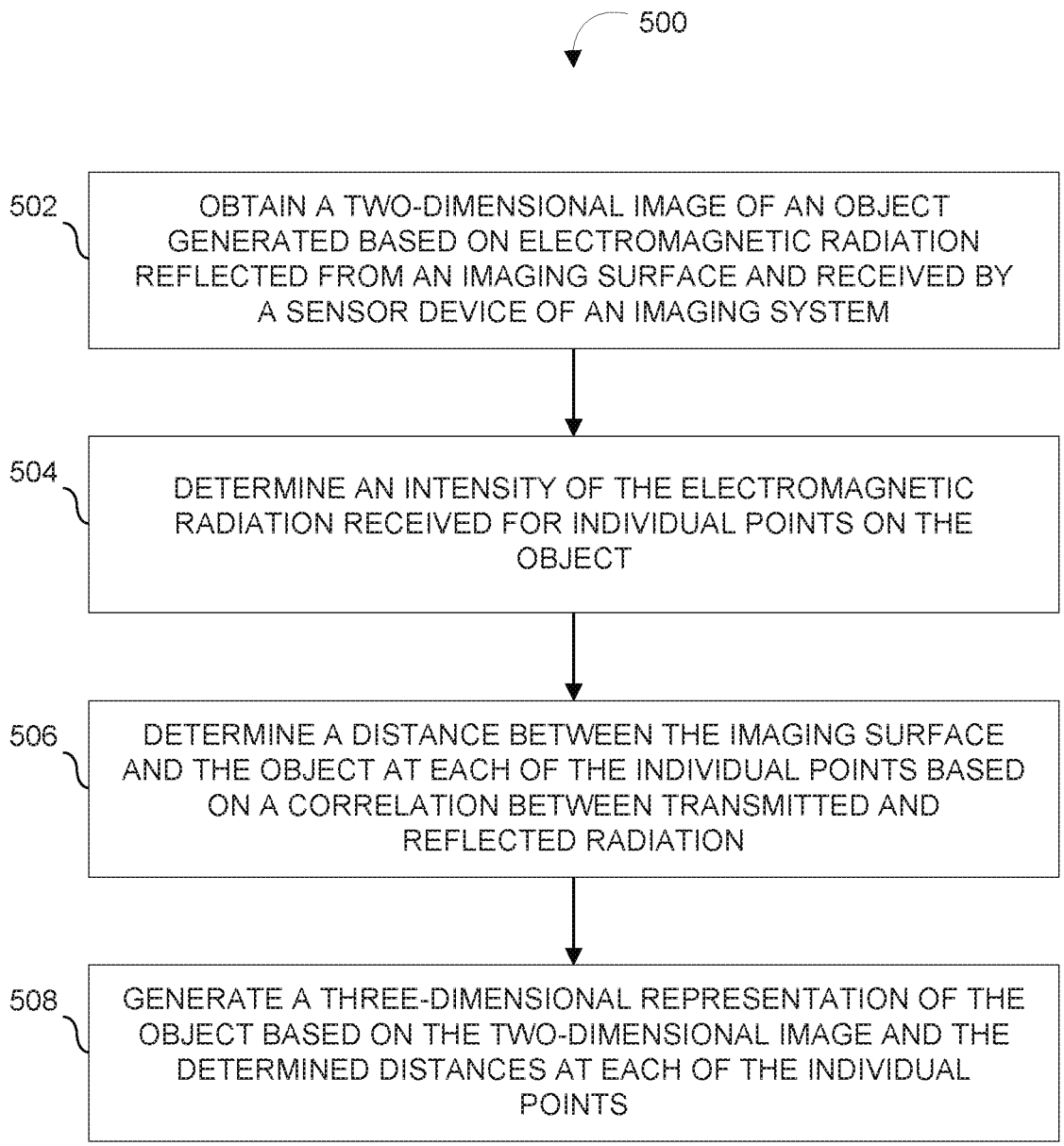
FIG. 5 illustrates a method for generating a three-dimensional image of a surface by measuring the amount of light that is reflected from the imaging surface after light transmitted due to broken TIR and frustrated total internal reflection has been removed, in accordance with one or more implementations.

FIG. 5 illustrates a method 500 for generating a three-dimensional image of a surface by measuring the amount of light that is reflected from the imaging surface after light transmitted due to broken TIR and frustrated TIR has been removed, in accordance with one or more implementations. The operations of method 500 presented below are intended to be illustrative and, as such, should not be viewed as limiting. In some implementations, method 500 may be accomplished with one or more additional operations not described, and/or without one or more of the operations discussed. For example, one or more additional processing steps may occur between obtaining a two-dimensional image of an object in operation 502 and generating a three-dimensional representation of the object in operation 508. In some implementations, two or more of the operations may occur substantially simultaneously. The described operations may be accomplished using some or all of the system components described in detail above.

In some implementations, method 500 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). The one or more processing devices may include one or more devices executing some or all of the operations of method 500 in response to instructions stored electronically on one or more electronic storage mediums. The one or more processing devices may include one or more devices configured through hardware, firmware, and/or software to be specifically designed for execution of one or more of the operations of method 500.

In an operation 502, method 500 may include obtaining a two-dimensional image of an object generated based on electromagnetic radiation reflected from an imaging surface and received by a sensor device of an imaging system. The two-dimensional image may comprise a two-dimensional image of an object in close proximity to an imaging surface. The two-dimensional image may be generated based on electromagnetic radiation reflected from the imaging surface and received by the sensor device of the imaging system. For example, a two-dimensional image of an object may be generated based on light received by a camera of a TIR-based imaging system. In some implementations, operation 502 may be performed by a processor component the same as or similar to information component 114 (shown in FIG. 1 and described herein).

In an operation 504, method 500 may include determining an intensity of the electromagnetic radiation that is received for individual points on the object. For example, the intensity of the electromagnetic radiation that is reflected from the imaging surface may be determined based on the radiation that is received by the sensor device. In various implementations, the intensity of the electromagnetic radiation that is received may be determined based on the two-dimensional image of the object. For example, in a TIR-based imaging system, the intensity of the light that is reflected from the imaging surface at individual points on the object may be determined based on the camera response of the camera of the TIR-based imaging system. In some implementations, operation 504 may be performed by a processor component the same as or similar to distance determination component 116 (shown in FIG. 1 and described herein).

In an operation 506, method 500 may include determining a distance between the imaging surface and the object at each of the individual points on the object. In various implementations, the distance between the imaging surface and the object at each of the individual points may be determined by measuring the amount of light that is reflected from the imaging surface after transmitted light due to the breakdown in TIR and the effects of FTIR have been removed. In other words, the distance between the imaging surface and the object at each of the individual points may be determined based on a correlation between the electromagnetic radiation transmitted towards the imaging surface and the electromagnetic radiation reflected from the imaging surface. The electromagnetic radiation that is reflected from the imaging surface for a given point on an object may be represented by the determined intensity of the radiation received for that point. In some implementations, operation 506 may be performed by a processor component the same as or similar to distance determination component 116 (shown in FIG. 1 and described herein).

In an operation 508, method 500 may include generating a three-dimensional representation of the object based on the two-dimensional image of the object and the determined distances between the imaging surface and the object at each of the individual points. In some implementations, operation 508 may be performed by a processor component the same as or similar to image generation component 118 (shown in FIG. 1 and described herein).

The systems and methods described herein relate to a novel device configured to generate a three-dimensional image of an object located on or in close proximity to an imaging surface. In various implementations, the object may comprise a finger or other human or animal skin. However, the object is not limited to a finger or other skin as the systems and methods described herein may be used to generate a three-dimensional image of any object that can be brought within close proximity to the imaging surface. For example, the systems and methods described herein may be used to generate a three-dimensional image of any object comprising at least one uneven surface.

For purposes of explanation, numerous specific details are set forth in order to provide a thorough understanding of the description. It will be appreciated by those having skill in the art that the implementations described herein may be practiced without these specific details or with an equivalent arrangement. Accordingly, it is to be understood that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

In some instances, well-known structures and devices are shown in block diagram form in order to avoid unnecessarily obscuring the description. In other instances, functional block diagrams and flow diagrams are shown to represent data and logic flows. The components of block diagrams and flow diagrams (e.g., modules, blocks, structures, devices, features, etc.) may be variously combined, separated, removed, reordered, and replaced in a manner other than as expressly described and depicted herein.

Reference in this specification to "one implementation", "an implementation", "some implementations", "various implementations", "certain implementations", "other implementations", "one series of implementations", or the like means that a particular feature, design, structure, or characteristic described in connection with the implementation is included in at least one implementation of the disclosure. The appearances of, for example, the phrase "in one implementation" or "in an implementation" in various places in the specification are not necessarily all referring to the same implementation, nor are separate or alternative implementations mutually exclusive of other implementations. Moreover, whether or not there is express reference to an "implementation" or the like, various features are described, which may be variously combined and included in some implementations, but also variously omitted in other implementations. Similarly, various features are described that may be preferences or requirements for some implementations, but not other implementations.

The language used herein has been principally selected for readability and instructional purposes, and it may not have been selected to delineate or circumscribe the inventive subject matter. Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system configured to generate a three-dimensional representation of a surface using frustrated total internal reflection, the system comprising:
   one or more physical computer processors configured by computer readable instructions to:
   obtain a two-dimensional image of an object in close proximity to an imaging surface, wherein the two-dimensional image is generated based on electromagnetic radiation reflected from the imaging surface and received by a sensor device of an imaging system;
   determine an intensity of the electromagnetic radiation received for individual points on the object;
   determine a distance between the imaging surface and the object at each of the individual points based on a correlation between the electromagnetic radiation transmitted towards the imaging surface and the electromagnetic radiation reflected from the imaging surface, wherein the determined intensity of the electromagnetic radiation indicates the electromagnetic radiation reflected from the imaging surface; and
   generate a three-dimensional representation of the object based on the two-dimensional image and the determined distances between the imaging surface and the object at each of the individual points.

2. The system of claim 1, wherein the electromagnetic radiation comprises light transmitted in a TIR-based imaging system towards the imaging surface which reflects the light toward the sensor device.

3. The system of claim 1, wherein the imaging system comprises one or more of a electroluminescent imaging system, an ultrasound scanner, a three-dimensional scanner, a capacitive array imaging system, a thermal sensor imaging system, a radio frequency (RF) imaging system, and/or a pressure sensor imaging system.

4. The system of claim 1, wherein the distance between the imaging surface and the object at each of the individual points is further determined based on one or more of an index of refraction of a first media through which the electromagnetic radiation is propagated, an index of refraction of a second media between the first media and the object, an index of refraction of the object, an angle of incidence at an interface between the first media and the second media, and/or a wavelength of the electromagnetic radiation transmitted towards the imaging surface.

5. The system of claim 1, wherein the one or more physical computer processors are further configured by computer readable instructions to:
   calculate the distance between the imaging surface and the object at each of the individual points; and
   generate a uniform point cloud indicating the distance between the imaging surface and the object at each of the individual points by adding a third spatial dimension to the two-dimensional image of the object.

6. The system of claim 5, wherein the three-dimensional representation of the object comprises a three-dimensional image of a surface of the object.

7. The system of claim 1, wherein the one or more physical computer processors are further configured by computer readable instructions to:
   segment the three-dimensional representation of the object based on a uniform point cloud; and
   identify one or more features of the object within the three-dimensional representation.

8. The system of claim 7, wherein the one or more physical computer processors are further configured by computer readable instructions to:
   determine feature measurements of the one or more of the features;
   generate a histogram of the feature measurements; and
   determine whether the object is real or fake based on the histogram.

9. A method for generating a three-dimensional representation of a surface using frustrated total internal reflection, the method being implemented by a computer system including one or more physical processors and storage media storing machine-readable instructions, the method comprising:
   obtaining a two-dimensional image of an object in close proximity to an imaging surface, wherein the two-dimensional image is generated based on electromagnetic radiation reflected from the imaging surface and received by a sensor device of an imaging system;
   determining an intensity of the electromagnetic radiation received for individual points on the object;
   determining a distance between the imaging surface and the object at each of the individual points based on a correlation between the electromagnetic radiation transmitted towards the imaging surface and the electromagnetic radiation reflected from the imaging surface, wherein the determined intensity of the electromagnetic radiation indicates the electromagnetic radiation reflected from the imaging surface; and
   generating a three-dimensional representation of the object based on the two-dimensional image and the determined distances between the imaging surface and the object at each of the individual points.

10. The method of claim 9, wherein the electromagnetic radiation comprises light transmitted in a TIR-based imaging system towards the imaging surface which reflects the light toward the sensor device.

11. The method of claim 9, wherein the imaging system comprises one or more of a electroluminescent imaging system, an ultrasound scanner, a three-dimensional scanner, a capacitive array imaging system, a thermal sensor imaging system, a radio frequency (RF) imaging system, and/or a pressure sensor imaging system.

12. The method of claim 9, wherein the distance between the imaging surface and the object at each of the individual points is further determined based on one or more of an index of refraction of a first media through which the electromagnetic radiation is propagated, an index of refraction of a second media between the first media and the object, an index of refraction of the object, an angle of incidence at an interface between the first media and the second media, and/or a wavelength of the electromagnetic radiation transmitted towards the imaging surface.

13. The method of claim 9, further comprising:
calculating the distance between the imaging surface and the object at each of the individual points; and
generating a uniform point cloud indicating the distance between the imaging surface and the object at each of the individual points by adding a third spatial dimension to the two-dimensional image of the object.

14. The method of claim 13, wherein the three-dimensional representation of the object comprises a three-dimensional image of a surface of the object.

15. The method of claim 9, further comprising:
segmenting the three-dimensional representation of the object based on a uniform point cloud; and
identifying one or more features of the object within the three-dimensional representation.

16. The method of claim 15, further comprising:
determining feature measurements of the one or more features;
generating a histogram of the feature measurements; and
determining whether the object is real or fake based on the histogram.

* * * * *